United States Patent
Sinha et al.

(10) Patent No.: US 9,259,479 B2
(45) Date of Patent: Feb. 16, 2016

(54) TREATMENT FOR COMORBID DIABETES WITH CHRONIC KIDNEY DISEASE

(71) Applicant: Eli Lilly and Company, Indianapolis, IN (US)

(72) Inventors: Vikram Paritosh Sinha, Carmel, IN (US); Melvin Jay Prince, Zionsville, IN (US); John Michael Beals, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/398,144

(22) PCT Filed: May 2, 2013

(86) PCT No.: PCT/US2013/039166
§ 371 (c)(1),
(2) Date: Oct. 31, 2014

(87) PCT Pub. No.: WO2013/169547
PCT Pub. Date: Nov. 14, 2013

(65) Prior Publication Data
US 2015/0111819 A1  Apr. 23, 2015

Related U.S. Application Data

(60) Provisional application No. 61/644,657, filed on May 9, 2012, provisional application No. 61/651,632, filed on May 25, 2012.

(51) Int. Cl.
| | | |
|---|---|---|
| A61K 38/16 | (2006.01) | |
| A61K 38/17 | (2006.01) | |
| A61K 38/28 | (2006.01) | |
| A61K 47/48 | (2006.01) | |
| A61K 38/22 | (2006.01) | |

(52) U.S. Cl.
CPC .......... *A61K 47/48215* (2013.01); *A61K 38/22* (2013.01); *A61K 38/28* (2013.01); *A61K 47/48* (2013.01); *A61K 47/48169* (2013.01)

(58) Field of Classification Search
None
See application file for complete search history.

(56) References Cited

FOREIGN PATENT DOCUMENTS

| EP | 0885961 | 12/1998 |
| WO | 2004091494 A2 | 10/2004 |
| WO | 2008084051 A1 | 7/2008 |
| WO | 2009152128 A1 | 12/2009 |

OTHER PUBLICATIONS

Iglesias et al., Diabetes, Obesity and Metabolism, (2008) 10, 811-823.*
Chelliah et al., Journal of Investigative Medicine (2004) 52(2), 104-108.*
Yadav, Subhash Chandra B. et al.,Glycemic control in diabetic kidney disease patients, Clinical Queries; Nephrology 0102, (2012) pp. 111-114.
Lubowsky, Noah et al., American Journal of Kidney Diseases, vol. 50, No. 5, Nov. 2007, pp. 865-879.

* cited by examiner

*Primary Examiner* — Marcela M Cordero Garcia
*Assistant Examiner* — Catherine Mader
(74) *Attorney, Agent, or Firm* — Duane C. Marks; James J. Kelley

(57) ABSTRACT

The present invention relates to an improved method for treating diabetes wherein the improvement comprises administering a PEGylated insulin compound to a patient having moderate to severe chronic kidney disease using an effective amount of the compound.

13 Claims, 1 Drawing Sheet

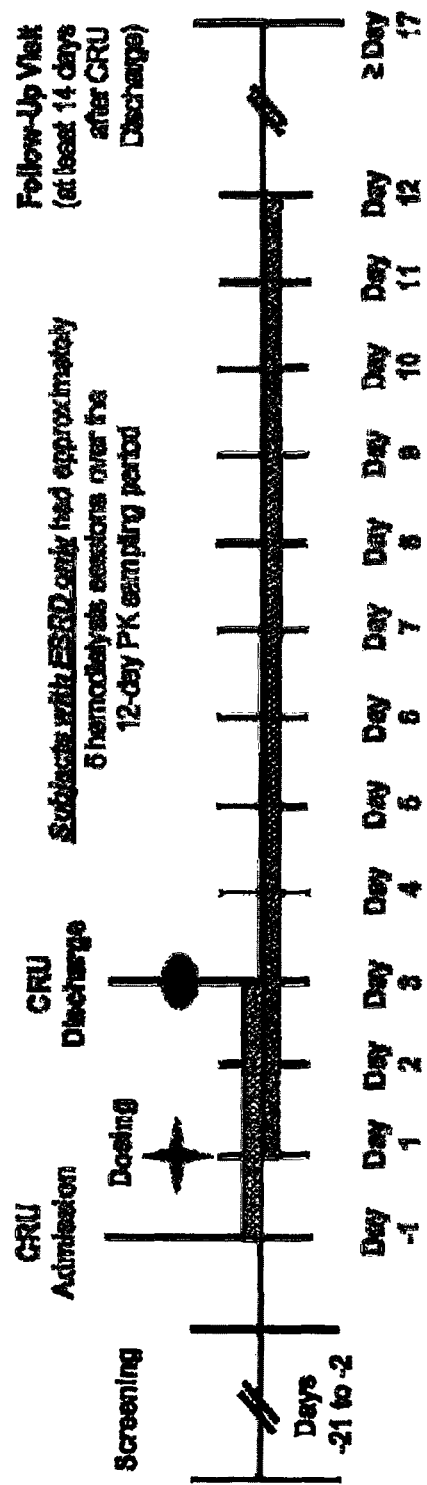

SEQUENCE LISTING

<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (28)..(28)
<223> OTHER INFORMATION: Lys at position 28 is modified with
      polyethylene glycol

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 3
<211> LENGTH: 30
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Lys at position 29 is modified with
      polyethylene glycol

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (6)..(11)

<400> SEQUENCE: 4

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 5
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is modified with
      polyethylene glycol

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 6
<211> LENGTH: 21
<212> TYPE: PRT
<213> ORGANISM: Bovine
<220> FEATURE:
<221> NAME/KEY: DISULFID
<222> LOCATION: (6)..(11)

<400> SEQUENCE: 6

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 7
<211> LENGTH: 30
<212> TYPE: PRT
<213> ORGANISM: Bovine
<220> FEATURE:
<221> NAME/KEY: MOD_RES
<222> LOCATION: (29)..(29)
<223> OTHER INFORMATION: Lys at position 29 is modified with
      polyethylene glycol

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is modified with
      polyethylene glycol

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

```
<210> SEQ ID NO 9
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (29)..(29)
<223> OTHER INFORMATION: Lys at position 29 is modified with
      polyethylene glycol

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Lys at position 3 is modified with
      polyethylene glycol

<400> SEQUENCE: 10

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```

TREATMENT FOR COMORBID DIABETES WITH CHRONIC KIDNEY DISEASE

This application is a national phase application under 35 U.S.C. §371 for PCT/US2013/039166, filed May 2, 2013, which claims the benefit under 35 U.S.C. Section 119 of U.S. Provisional Patent Applications 61/651632, filed May 25, 2012, and U.S. Provisional Application 61/644,657 filed May 9, 2012.

The present invention is in the field of medicine, particularly in the field of treating diabetes with comorbid chronic kidney disease (CKD) using insulins. The invention provides a method of treatment for patients' diabetes with CKD.

Treatment of hyperglycemia in patients with declining renal function or diabetes in patients with diabetic nephropathy-CKD (DN-CKD) is particularly vexing once the Glomular Filtration Rate (GFR) declines to <60 mL/min/1.72 m². These patients often experience clinically significant variations in the time action profile of insulin, increased hypoglycemic events, poorly controlled glucose levels, and insulin induced edema requiring frequent blood glucose monitoring, insulin dose adjustments, and intense health care provider intervention in an attempt to balance glucose control with the significant risk for hypoglycemia. Patients with DN-CKD have increased risks for hypoglycemia for two reasons: (1) decreased clearance of insulin and (2) impaired kidney gluconeogenesis. With reduced kidney mass, the amount of gluconeogenesis carried out by the kidney is decreased. The reduction in gluconeogenesis may reduce the ability of a patient who is becoming hypoglycemic as the result of excessive insulin dosage or lack of food intake to defend against hypoglycemia. Approximately 30-70% of exogenous insulin clearance is carried out by the kidney, and impaired kidney function is associated with a prolonged half-life of administered insulin. A group of Type 1 diabetes patients with DN-CKD who were using exogenous insulin had a 5-fold increase in the frequency of severe hypoglycemia and Type 2 diabetes patients with DN-CKD had a significant increase in the frequency of severe hypoglycemia. Therefore, it is imperative that patients being treated using insulin intensively monitor their glucose levels closely and reduce doses of medicines (insulin and oral agents) as needed to avoid hypoglycemia. The risk of serious hypoglycemic event is a significant concern due to the tiredness, headache, confusion, or even unconsciousness and death associated with severe hypoglycemia. A further complication associated with insulin treatment for DN-CKD is insulin-induced edema.

Intensive glucose control is reported to decrease microvasculature diabetic complications when compared with conventional glucose control; however, the increased risk for severe hypoglycemic events in patients with DN-CKD makes intensive glucose control difficult, if not impossible, to achieve. Patients with DN-CKD are often treated using insulin; however, the varying kidney function and gluconeogenesis confounds the insulin dosing regimen, with the need for intense blood glucose monitoring, insulin adjustment, and surveillance to avoid severe hypoglycemia. Long duration of action insulins, referred to as basal insulins, can be particularly difficult for patients with declining renal function and may be particularly difficult for Type 1 diabetes patients. For example, the safety section of insulin glargine labeling states that insulin glargine is not recommended during periods of rapidly declining renal function because of the risk for prolonged hypoglycemia. Insulin glargine was not studied in patients with DN-CKD prior to its approval and is currently being studied in Type 2 diabetes patients with dose adjustments. ("Evaluation of the Safety and Efficacy of Insulin Glargine+Glulisine or Insulin Regular+NPH Insulins (Isophane insulin) Use in Type 2 Diabetes Mellitus Patients with Moderate Renal Failure" (recruiting patients; verified April 2012 by Sanofi-Aventis) and "Glargine Dosing in Hospitalized Patients With Type 2 Diabetes and Renal Insufficiency" (recruiting patients; Verified September 2011 by Loyola University). Current treatment guidelines are set forth by the Kidney Disease Outcomes Quality Initiative at http://www.kidney.org/professionals/KDOQI/guideline_diabetes/ (©2007 National Kidney Foundation) wherein, the National Kidney Foundation recommends intensive glucose control; however, the guidelines add that the major risk for patients is hypoglycemia. Accordingly, intensive monitoring and dose adjustment, beyond those required for the normal patient with diabetes, is imperative; however in spite of these efforts, insulin-induced edema may result despite intensive monitoring and dose adjustment.

Hypoglycemia in patients with DN-CKD is particularly challenging when a patient first present themself in a clinical setting with severe hyperglycemia and the patient usually presents with no knowledge of their declining renal function. The health care professional is forced to empirically deconvolute the renal function through experimentation with insulin doses and close monitoring of the glucose levels to avoid hypoglycemia.

There is a need for a treatment for patients with DN-CKD that can provide intensive glucose control with standard dosing similar to dosing used for the normal diabetes patient having normal renal function. There is a need for a treatment method for patients with moderate or severe DN-CKD wherein the insulin is administered without dose reduction based on the level of renal impairment. There is a need for a treatment method for DN-CKD patients that can provide intensive glucose control with an incidence of hypoglycemia that is comparable to that observed in the diabetic patient with normal renal function. There is a need for a treatment method for DN-CKD that can attenuate insulin induced edema.

PEGylated insulin lispro having an extended profile of action for the treatment of diabetes is described in WO 2009/152128. The treatment of diabetes is generally described; however, the treatment of patients suffering from DN-CKD and diabetes is not specifically described. The present invention provides a treatment method that is particularly effective in this select patient group and offers unexpected advantages to these patients. Prior to this invention, diabetes patients with moderate or severe DN-CKD were particularly vexing to treat.

The present invention provides a method for treating diabetes in a patient having moderate to end-stage chronic kidney disease comprising administering to said patient a compound of the formula P-[(A)-(B)] wherein:

A is the A-chain of insulin lispro (SEQ ID NO: 1);
B is the B-chain of insulin lispro (SEQ ID NO: 2); and
P is a PEG having an average molecular weight from about 17.5 kDa to about 40 kDa, and wherein A and B are properly cross-linked, and P is attached via a covalent bond to the epsilon amine of the lysine at position 28 of B.

The present invention provides a method of treating hyperglycemia in a patient having moderate to end-stage chronic kidney disease comprising administering to said patient a compound of the formula P-[(A)-(B)] wherein:

A is the A-chain of insulin lispro (SEQ ID NO: 1);
B is the B-chain of insulin lispro (SEQ ID NO: 2); and
P is a PEG having an average molecular weight from about 17.5 kDa to about 40 kDa, and wherein A and B are properly cross-linked, and P is attached via a covalent bond to the epsilon-amine of the lysine at position 28 of B.

The present invention provides a method for treating diabetes in a patient having moderate to end-stage chronic kidney disease, comprising administering to said patient a compound of the formula P-[(A$^a$)-(B$^a$)] wherein:
- A$^a$ is the A-chain selected from the group consisting of the A-chain of human insulin (SEQ ID NO: 1), the A-chain of insulin glargine (SEQ ID NO: 4), and the A-chain of bovine insulin (SEQ ID 6);
- B$^a$ is the B-chain selected from the group consisting of the B-chain of human insulin (SEQ ID NO: 3), B-chain of des-B30 insulin (SEQ ID NO: 8), porcine insulin (SEQ ID NO: 7), B-chain of insulin aspart (SEQ ID NO: 9), B-chain of insulin glargine (SEQ ID NO: 5), and B-chain of bovine insulin (SEQ ID NO: 7); and P is a PEG having an average molecular weight from about 17.5 kDa to about 40 kDa, and wherein A$^a$ and B$^a$ are properly cross-linked, and P is attached via a covalent bond to the epsilon amine of the lysine at position 29 of B$^a$.

The present invention provides a method for treating hyperglycemia in a patient having moderate to end-stage chronic kidney disease, comprising administering to said patient a compound of the formula P-[(A$^a$)-(B$^a$)] wherein:
- A$^a$ is the A-chain selected from the group consisting of A-chain of human insulin (SEQ ID NO: 1), A-chain of insulin glargine (SEQ ID NO: 4), and A-chain of bovine insulin (SEQ ID 6);
- B$^a$ is the B-chain selected from the group consisting of B-chain of human insulin (SEQ ID NO: 3), B-chain of des-B30 insulin (SEQ ID NO: 8), B-chain of porcine insulin (SEQ ID NO: 7), insulin aspart (SEQ ID NO: 9), B-chain of insulin glargine (SEQ ID NO: 5), and B-chain of bovine insulin (SEQ ID NO: 7); and P is a PEG having an average molecular weight from about 17.5 kDa to about 40 kDa, and wherein A$^a$ and B$^a$ are properly cross-linked, and P is attached via a covalent bond to the epsilon amine of the lysine at position 29 of B$^a$.

The present invention provides a method for treating diabetes in a patient having moderate to end-stage chronic kidney disease, comprising administering to said patient a compound of the formula P-[(A$^b$)-(B$^b$)] wherein:
- A$^b$ is the A-chain of insulin (SEQ ID NO: 1)
- B$^b$ is the B-chain of insulin glulisine (SEQ ID NO: 10); and P is a PEG having an average molecular weight from about 17.5 kDa to about 40 kDa, and wherein A$^b$ and B$^b$ are properly cross-linked, and P is attached via a covalent bond to the epsilon amine of the lysine at position 3 of B$^b$.

The present invention provides a method for treating hyperglycemia in a patient having moderate to end-stage chronic kidney disease, comprising administering to said patient a compound of the formula P-[(A$^b$)-(B$^b$)] wherein:
- A$^b$ is the A-chain of insulin (SEQ ID NO: 1)
- B$^b$ is the B-chain of insulin glulisine (SEQ ID NO: 10); and P is a PEG having an average molecular weight from about 17.5 kDa to about 40 kDa, and wherein A$^b$ and B$^b$ are properly cross-linked, and P is attached via a covalent bond to the epsilon amine of the lysine at position 3 of B$^b$.

The present invention also provides the use of a compound of the formula P-[(A)-(B)] in the manufacture of a medicament for the treatment of diabetes in a patient with moderate to end-stage chronic kidney disease, wherein:
- A is the A-chain of insulin lispro (SEQ ID NO:1);
- B is the B-chain of insulin lispro (SEQ ID NO:2); and P is a PEG having an average molecular weight from about 17.5 kDa to about 40 kDa, and wherein A and B are properly cross-linked, and P is attached via a urethane bond to the epsilon amine of the lysine at position 28 of B.

The present invention also provides the use of a compound of the formula P-[(A)-(B)] in the manufacture of a medicament for the treatment of hyperglycemia in a patient with moderate to end-stage chronic kidney disease wherein:
- A is the A-chain of insulin lispro (SEQ ID NO:1);
- B is the B-chain of insulin lispro (SEQ ID NO:2); and P is a PEG having an average molecular weight from about 17.5 kDa to about 40 kDa, and wherein A and B are properly cross-linked, and P is attached via a urethane bond to the epsilon amine of the lysine at position 28 of B.

The present invention provides the use of a compound of the formula P-[(A$^a$)-(B$^a$)] in the manufacture of a medicament for the treatment of diabetes in a patient with moderate to end-stage chronic kidney disease wherein:
- A$^a$ is the A-chain selected from the group consisting of human insulin (SEQ ID NO:1), insulin glargine (SEQ ID NO:4), and bovine insulin (SEQ ID 6);
- B$^a$ is the B-chain selected from the group consisting of human insulin (SEQ ID NO: 3), des-B30 insulin (SEQ ID NO: 8), porcine insulin (SEQ ID NO: 7), insulin aspart (SEQ ID NO: 9), insulin glargine (SEQ ID NO: 5), and bovine insulin (SEQ ID NO: 7); and P is a PEG having an average molecular weight from about 17.5 kDa to about 40 kDa, and wherein A$^a$ and B$^a$ are properly cross-linked, and P is attached via a covalent bond to the epsilon amine of the lysine at position 29 of B$^a$.

The present invention provides the use of a compound of the formula P-[(A$^a$)-(B$^a$)] in the manufacture of a medicament for the treatment of hyperglycemia in a patient with moderate to end-stage chronic kidney disease wherein:
- A$^a$ is the A-chain selected from the group consisting of human insulin (SEQ ID NO:1), insulin glargine (SEQ ID NO:4), and bovine insulin (SEQ ID 6);
- B$^a$ is the B-chain selected from the group consisting of human insulin (SEQ ID NO: 3), des-B30 insulin (SEQ ID NO: 8), porcine insulin (SEQ ID NO: 7), insulin aspart (SEQ ID NO: 9), insulin glargine (SEQ ID NO: 5), and bovine insulin (SEQ ID NO: 7); and P is a PEG having an average molecular weight from about 17.5 kDa to about 40 kDa, and wherein A$^a$ and B$^a$ are properly cross-linked, and P is attached via a covalent bond to the epsilon amine of the lysine at position 29 of B$^a$.

The present invention provides the use of a compound of the formula P-[(A$^b$)-(B$^b$)] in the manufacture of a medicament for the treatment of diabetes in a patient with moderate to end-stage chronic kidney disease wherein:
- A$^b$ is the A-chain of insulin (SEQ ID NO:1)
- B$^b$ is the B-chain of insulin glulisine (SEQ ID NO:10); and
- P is a PEG having an average molecular weight from about 17.5 kDa to about 40 kDa, and wherein A$^b$ and B$^b$ are properly cross-linked, and P is attached via a covalent bond to the epsilon amine of the lysine at position 3 of B$^b$.

The present invention provides the use of a compound of the formula P-[(A$^b$)-(B$^b$)] in the manufacture of a medicament for the treatment of hyperglycemia in a patient with moderate to end-stage chronic kidney disease wherein:
- A$^b$ is the A-chain of insulin (SEQ ID NO:1)
- B$^b$ is the B-chain of insulin glulisine (SEQ ID NO:10); and P is a PEG having an average molecular weight from about 17.5 kDa to about 40 kDa, and wherein A$^b$ and B$^b$ are properly cross-linked, and P is attached via a covalent bond to the epsilon amine of the lysine at position 3 of B$^b$.

The present invention provides the use of a compound of the formula P-[(A)-(B)] in the manufacture of a medicament for the treatment of insulin induced edema wherein:
- A is the A-chain of insulin lispro (SEQ ID NO:1);
- B is the B-chain of insulin lispro (SEQ ID NO:2); and P is a PEG having an average molecular weight from about 17.5 kDa to about 40 kDa, and wherein A and B are properly cross-linked, and P is attached via a urethane bond to the epsilon amine of the lysine at position 28 of B.

BRIEF DESCRIPTION OF THE DRAWINGS

FIG. 1 is a schematic of the clinical design as described in Example 2.

Although the instant drawing may be useful in understanding, illustrating and/or explaining one or more embodiments of the instant disclosure, the drawing is not necessarily to scale and should not be construed as limiting the disclosure in any manner.

As used herein "an effective amount" means that the dosage of the compound is determined independent from the patient's renal function status and the dosage and administration of the PEGylated insulin compound is determined without dose reduction based on renal impairment. That is, the dosing regimen is consistent with the dosing regimen for the PEGylated insulin compound for a comparable diabetes patient having normal renal function.

Compounds administered in the present invention are PEGylated insulin compounds. As used herein, "PEGylated insulin compound" refers to a compound selected from the group consisting of the formula P-[(A)-(B)], P-[($A^a$)-($B^a$)], and P-[($A^b$)-($B^b$)], wherein: A, $A^a$, and $A^b$ each mean the A-chain. B, $B^a$, and $B^b$ each means the B-chain. P is a polyethylene glycol moiety having an average molecular weight from 17.5 kDa to 40 kDa, and wherein the A-chain and the B-chain are properly cross-linked. In one embodiment, the B-chain is the B-chain of insulin lispro (SEQ ID NO: 2) and P is attached via a covalent bond to the epsilon amine of the lysine at position 28 of B. In one embodiment, $B^b$) is the B-chain of insulin glulisine (SEQ ID NO: 10) and P is attached via a covalent bond to the epsilon amine of the lysine at position 3 of $B^b$. In another embodiment, the $B^a$ is selected from the group consisting of the B-chain of human insulin (SEQ ID NO: 3), the B-chain of des-B30 insulin (SEQ ID NO: 8), the B-chain of insulin glargine (SEQ ID NO: 5), the B-chain of insulin aspart (SEQ ID NO: 9), the B-chain of porcine insulin (SEQ ID NO: 7), and the B-chain of bovine insulin (SEQ ID NO: 7) and P is attached via a thioether or urethane bond to the epsilon amine of the lysine at position 29 of $B^a$. One preferred embodiment is P-[(A)-(B)], wherein P has an average molecular weight from 17.5 kDa to 30 kDa; in another embodiment, from 17.5 kDa to 25 kDa; in another embodiment, from 18 kDa to 22 kDa; in another embodiment, from 19 kDa to 21 kDa; in another embodiment, from 18 kDa to 21 kDa; in another embodiment, from 20 kDa to 40 kDa; in another embodiment, from 18 kDa to 20 kDa; and in another embodiment, 20 kDa. One preferred embodiment is PEGylated insulin for treating patients with DN-CKD wherein the PEGylated insulin is $PEG_{20\,kDa}$-LysB28 insulin lispro, shown as follows:

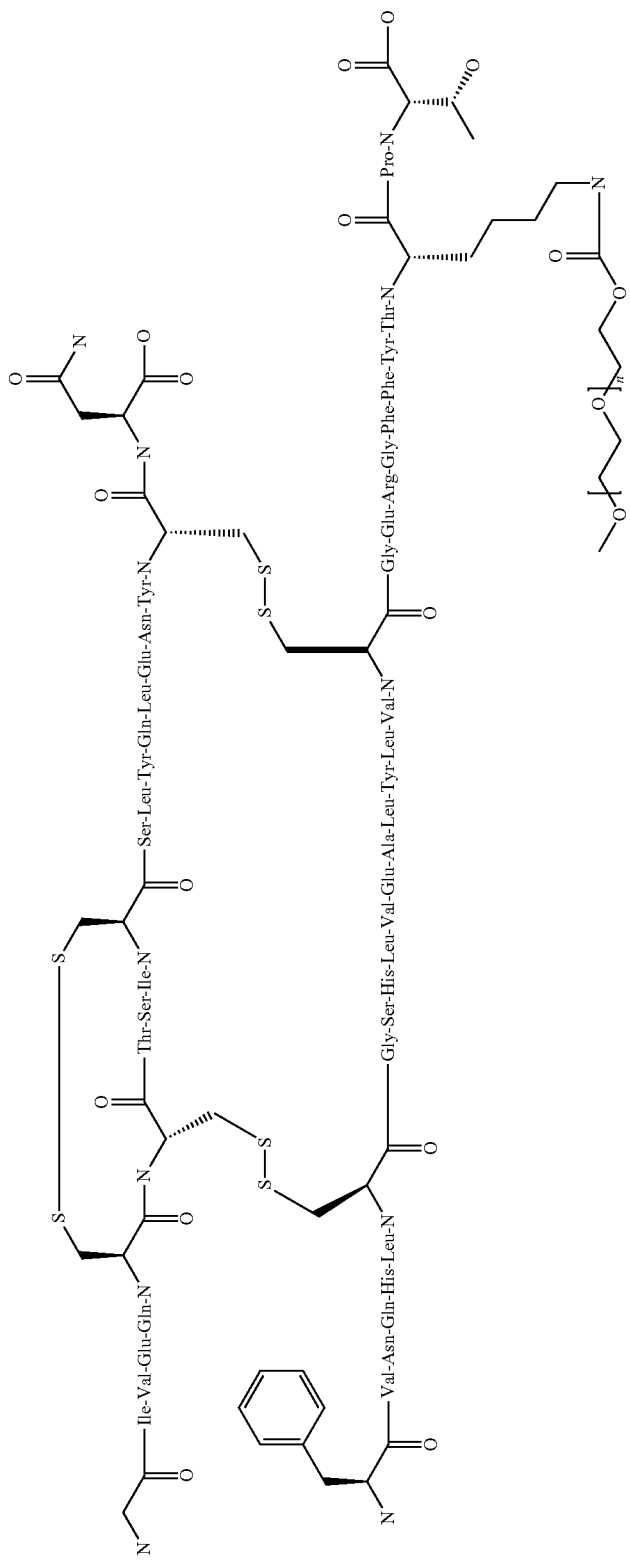

wherein n is about 406 to about 497, most preferably n is about 452.

As used herein, "cross-linked" means disulfide bonds exist between cysteine residues. "Properly cross-linked" as used herein refers to an insulin compound that contains a disulfide bond between the cysteine at position 7 of the A-chain (SEQ ID NO:1) and the cysteine at position 7 of the B-chain (SEQ ID NO:2), between the cysteine at position 20 of the A-chain (SEQ ID NO:1) and the cysteine at position 19 of the B-chain (SEQ ID NO:2), and between the cysteine at position 6 of the A-chain (SEQ ID NO:1) and the cysteine at position 11 of the A-chain (SEQ ID NO:1). The insulin will contain the three, correctly positioned disulfide bridges in human insulin, i.e., between $Cys^{A7}$ and $Cys^{B7}$, between $Cys^{A20}$ and $Cys^{B19}$ and between $Cys^{A6}$ and $Cys^{A11}$. It is recognized to one skilled in the art, the exact numerical designations may vary from species-to-species due to insertion and deletions that have occurred during evolution; however, the residues involved in the insulin cross-linking remained conserved across species as identified in sequence alignments.

The term "polyethylene glycol" or "PEG" refers to a PEG compound or derivative thereof, with or without coupling agents or derivatization with coupling or activating moieties or derivatization with a capping group at one end. In its typical form, PEG is a linear polymer with terminal hydroxyl groups and has the formula HO—$CH_2CH_2$—$(CH_2CH_2O)_n$—$CH_2CH_2$—OH. In another form, PEG is a linear polymer with one terminal capped with a methoxy group and the other terminal capped with an activating group, e.g., p-nitrophenyl carbonate; thus having a formula

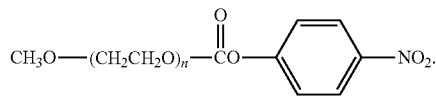

The number of repeating subunits "n" in the PEG is approximated from the molecular mass described in Daltons. Typically, PEG reagents used to prepare PEGylated compounds comprise a heterogenous mixture of PEGs having a different number (n) of ethylene glycol subunits in the PEG polymer. A single ethylene glycol subunit (—$(CH_2CH_2O)$) of PEG has a molecular weight of about 44 Daltons. Therefore, the molecular weight of the PEG polymer depends on the number (n). The PEGs attached to the PEGylated insulin compounds of the present invention will have n in the range from about 400 to about 1000 subunits. In a preferred embodiment, the PEG attached to the PEGylated insulin compound of the present invention will have n in the range from about 400 to 750. In a more preferred embodiment, the PEG attached to the PEGylated insulin lispro compound of the present invention will have n in the range from about 400 to about 550. In a preferred embodiment, the PEG attached to the PEGylated insulin compound of the present invention will have n of about 400 and about 500.

Because PEGs are typically generated and used as mixtures of PEG compounds varying to some degree in their molecular weight, one of ordinary skill in the art generally describes the molecular weight of a PEG attached to a compound by describing the average size of the PEG reagent used in the PEGylation reaction that generated the particular PEGylated compound. Among the many possible ways of reporting averages, three are commonly used: the number-average, weight-average, and z-average molecular weights. As used herein, the phrase "average molecular weight" is intended to refer to the weight-average molecular weight which can be measured using techniques well-known in the art including, but not limited to, matrix-assisted laser desorption ionization time of flight (MALDI-TOF) mass spectrometry, gel permeation chromatography, or other liquid chromatography techniques, light scattering techniques, ultracentrifugation, and viscometry. The formula for calculating weight-average molecular weight may be represented as $\Sigma(M_i^2 N_i)/\Sigma(M_i N_i)$ where $N_i$ is the mole-fraction (or the number-fraction) of molecules with molecular weight $M_i$ in the mixture. The formula for calculating number-average molecular weight may be represented as $\Sigma(M_i N_i)/\Sigma(N_i)$ where $N_i$ is the mole-fraction (or the number-fraction) of molecules with molecular weight $M_i$ in the mixture. The ratio of weight-average molecular weight and number-average molecular weight is known as the polydispersity index ("PDI"), and provides a rough indication of the breadth of the distribution. The PEG reagents suitable for preparing the PEGylated insulin lispro compounds administered in the present invention are typically polydisperse (i.e., number-average molecular weight and weight-average molecular weight of the polymers are not equal). Preferably, the PDI for PEG reagents used to prepare the compounds administered in the present invention is less than about 1.1, more preferably, less than about 1.05.

The invention provides a mono-PEGylated insulin lispro compound comprising a PEG having an average molecular weight of 17.5 kDa, 20 kDa, 25 kDa, 30 kDa, or 40 kDa covalently attached directly or indirectly to the epsilon amine of the lysine at position 28 of the B-chain of insulin lispro. In a preferred embodiment, the mono-PEGylated insulin lispro comprises a PEG having an average molecular weight of 17.5 kDa, 20 kDa, 25 kDa, 30 kDa, or 40 kDa attached either directly or indirectly to the epsilon amine of the lysine at position 28 of the B-chain of insulin lispro. In a preferred embodiment, the mono-PEGylated insulin lispro comprises a PEG having an average molecular weight of 17.5 kDa to 25 kDa, 30 kDa, or 40 kDa attached to the epsilon-amine of the lysine at position 28 of the B-chain of insulin lispro. In another preferred embodiment, the mono-PEGylated insulin lispro comprises a PEG having an average molecular weight of 17.5 kDa or 20 kDa attached to the epsilon amine of the lysine at position 28 of the B-chain of insulin lispro ($PEG_{20\ kDa}$-LysB28 insulin lispro). In a particularly preferred embodiment, the mono-PEGylated insulin lispro comprises a PEG having an average molecular weight of 20 kDa attached to the epsilon amine of the lysine at position 28 of the B-chain of insulin lispro (i.e., $PEG_{20\ kDa}$-LysB28 insulin lispro).

The term "covalent bond" refers to a covalent bond providing desired stability and lability for the insulin. In a preferred embodiment, the covalent bond is a thioether or urethane bond. In another preferred embodiment, the covalent bond is a urethane bond.

Methods for preparing PEGylated insulin lispro and salts thereof are known and as described in WO 2009/152128. Methods for formulating PEGylated insulin lispro and salts thereof are known and as described in WO 2009/152128. The PEGylated insulin lispro as used in the treatment of diabetes in patients with DN-CKD may be administered in a sequentially or concomitantly with a rapid-acting insulin formulation or fast-acting insulin analog formulation.

Insulins that contain a single epsilon amine, i.e., a single lysine, can be selectively modified and purified as described in WO 2009/152128. Specifically, the ability to alter reactivity available amines by adjusting the pH to alkaline conditions facilitates the selective PEGylation of the epsilon amine of lysine with p-nitrophenylcarbonate-activated PEG. It is recognized one skilled in the art that the degree of multiple PEGylation can also be minimized by controlling the amount of excess PEG used in the reaction mixture. Lastly, the implementation of a chromatography step or steps, e.g., size chromatography, ion exchange chromatography, reversed-phase chromatography, and/or hydrophobic chromatography, can be used to isolate the mono-PEGylated species from di- and tri-PEGylated species.

A therapeutically effective amount is an amount of an active agent necessary to impart a therapeutic benefit to the patient. It will be understood that the amount of active agent actually administered will be determined by a physician and/or patient, in light of the relevant circumstances for treatment using a basal insulin, including the chosen route of administration, the actual active agent administered, the age, weight, and response of the individual patient, and the severity of the patient's symptoms. Certain dosing regimens provide once daily or less frequent administration or more frequent administration. Commercially available insulin labels generally recommend dose adjustment and frequent blood glucose monitoring in renal patients; however, the effective amount of PEGylated insulin lispro for treating diabetes in patients with DN-CKD will be within the a typical range of doses utilized by diabetes patient with normal renal function; thus, eliminating the need to empirically deconvolute the degree of declining renal clearance through frequent dose adjustment to minimize hypoglycemic events.

"DN-CKD" as used herein means a patient having comorbid chronic kidney disease with diabetes. "comorbid chronic kidney disease" or "kidney disease" as used herein means a patient diagnosed with chronic kidney disease, and is generally based on creatinine clearance characterized as moderate (CLcr 30-59 mL/min), severe (CLcr 15-29 mL/min), and/or end stage renal disease (requiring dialysis). As used herein "DN-CKD" contemplates both 1) a patient presenting with declining renal function and secondary diabetes or 2) a patient presenting with diabetes and diagnosed with secondary declining renal function resulting in chronic kidney disease; wherein the patient may or may not be diagnosed with diabetic nephropathy. The comorbid chronic kidney disease in one embodiment is "DN-CKD". The comorbid chronic kidney disease in one embodiment is kidney disease characterized as moderate (CLcr 30-59 mL/min) or severe (CLcr 15-29 mL/min) In one embodiment the chronic kidney disease is characterized as kidney disease with rapidly declining renal function. "Diabetes" or "diabetes mellitus" refers to a group of metabolic diseases characterized by high blood glucose levels, resulting from the inability of the body to either produce and/or use insulin. As used herein, "diabetes" includes type 1 diabetes mellitus or insulin-dependent diabetes mellitus, type 2 diabetes mellitus or non-insulin-dependent diabetes, and gestational diabetes.

As used herein, "hyperglycemia" is a condition in which an excessive amount of blood glucose circulates in the body. Hyperglycemia can be fasting hyperglycemia, which is defined as blood sugar greater than about 126 mg/dL (7.0 mmol/L) after fasting for at least 8 hours. Alternatively, hyperglycemia can be postprandial hyperglycemia, which is defined as blood sugar greater than about 180 mg/dL (10 mmol/L).

"Hypoglycemia" is a condition characterized by a low level of glucose in the blood, typically when glucose levels fall below 70 mg/dL. The incidence of hypoglycemia is measured by the percentage of patients experiencing at least one occurrence when a patient's glucose level remains at or below 70 mg/dL in a group of patients with diabetes for a given time period. The risk for hypoglycemia is determined by the percentage of individuals experiencing at least one episode of hypoglycemia during a given time period. The risk of hypoglycemia is determined by comparing the incidence, typically measured as a percentage, in the patient with DN-CKD versus that of a comparable group of diabetes patients having normal renal function during a similar time period.

As used herein, "hemoglobin A1c", "$Hb_{A1c}$", or "A1c" refers to glycosylated hemoglobin. Hemoglobin A1c is utilized to identify the average plasma glucose concentration over prolonged periods of time. This clinical analyte provides an estimate of a patient's average blood glucose level over the past two to three months. "Intense Glucose Control" targets lowering the DN-CKD patients $HB_{A1c}$ levels to 7% or less.

The terms "treatment", "treat", or "treating" as used herein refers to the management and care of a patient with DN-CKD for the purpose of combating or alleviating hyperglycemia and complications of the condition. These terms include administering PEGylated insulin compounds used in the present invention to attenuate or prevent the onset of certain symptoms or complications commonly observed in a patient with DN-CKD. A preferred treatment goal is clinically acceptable glycemic control in a patient with DN-CKD using doses that may be established without reduction based on the patient's renal impairment. Treatment will offer consistent time action of PEGylated insulin in the patient with DN-CKD across populations having varying renal function. Consistent time action, independent of variability due to renal clearance, provides the patient and healthcare professional greater confidence to aggressively treating the patient's diabetes with comorbid DN-CKD. The aggressive treatment generally provides better glycemic outcomes and attenuation of comorbidities, with a concomitant reduction in hypoglycemia. Treatment may attenuate insulin related edema in DN-CKD. Treatment may attenuate hypoglycemic episodes in the DN-CKD patient. The patient to be treated is a mammal A preferred patient in one embodiment is a human. A preferred patient in one embodiment is a dog or a cat.

As used herein, "peak-to-trough fluctuation" or "PTF" refers to the ratio of serum concentration of PEGylated insulin lispro measured at its peak concentration divided by the serum concentration of the same PEGylated insulin measured at its lowest concentration (nadir) during a dosing interval. It is assessed by determining the ratio of $C_{max}$ at steady-state relative to the minimum observed drug concentration, the nadir, during a dosing interval at steady-state.

A PTF of 1 is a flat line (i.e., peakless). The closer the PTF is to a value of 1, the more consistent the blood glucose level is; however, a PTF value of no more than 2 is considered consistent and may provide a greater percentage of patients in a group of DN-CKD patients with $HB_{A1c}$ levels that are 7% or less. In a preferred embodiment, the PTF value is less than 1.75. In a more preferred embodiment, the PTF value is less than 1.5.

As used herein "consistent time action" means that the average PTF of the basal insulin at steady-state in a group of patients with DN-CKD is less than the average PTF would be for a comparable group of patients with DN-CKD, having comparable renal function at a similar time in the dosing interval, with insulin glargine treatment. Accordingly, in a group of comparable patients with DN-CKD at a similar time in the dosing interval, the percentage of patients reaching intense glucose control with $HB_{A1c}$ levels that are 7% or less is likewise, greater in the PEGylated insulin treatment group than in the insulin glargine treatment group. Generally, "PTF" value is not more than 2 for a given dosing interval. In a preferred embodiment using $PEG_{20\ kDa}$-LysB28 insulin lispro the PTF value is less than 1.5.

As used herein, "attenuated hypoglycemia" means that for a given time period in a group of comparable patients with DN-CKD, the total amount of time that the patient's blood glucose level was below 70 mg/dL at steady-state is statistically significantly less than would have been experienced by the comparable group of patients with DN-CKD having comparable renal function during the same given time period, to obtain an equivalent or substantially equivalent level of glycemic control, utilizing insulin glargine or human insulin treatment.

Pharmaceutical compositions comprising a PEGylated insulin, according to the present invention, may be administered parenterally to a patient with DN-CKD in need of such a treatment. Parenteral administration may be performed by subcutaneous, intramuscular, or intravenous injection by means of a syringe, optionally a pen-like syringe, or mechanical driven injector. Alternatively, parenteral administration can be performed by means of an infusion pump. In a preferred embodiment, the PEGylated insulin is PEGylated insulin lispro administered parenterally to a patient with DN-CKD in need of such treatment. In a preferred embodiment, the PEGylated insulin lispro is administered to a type 1 diabetes patient with DN-CKD. In a preferred embodiment, the PEGylated insulin lispro is administered to a type 2 diabetes patient with DN-CKD.

The PEGylated insulin compounds and compositions of the invention may be formulated analogously with known formulations of the insulins that are administered to patients parenterally. In a preferred embodiment the PEGylated insulin is PEGylated insulin lispro is co-formulated or extemporaneously mixed with insulin lispro. Such formulations are known to one skilled in the art.

Example 1

⅚ Nephrectomized Rat Study

Sprague Dawley male rats undergo a two part nephrectomy (⅚) surgery (surgeries separated by 1 week). Sham surgery animals are also prepared. Animals are monitored daily for health during the 5 week time frame that allows progression of the disease state to ⅙th of normal renal function. To study the impact of renal clearance, ⅚ and sham animals (N=8-10) are administered test article at a dose of 10 nmol/kg via penile vein injections (1 ml/kg). Blood samples are collected at 1, 2, 4, 8, 15, 25, 40 and 80 minutes post lispro insulin injection; 2, 10, 30, 60, 90, 120, 150 and 180 minutes post $PEG_{5K}$-LysB28 insulin lispro injection; 2, 10, 30, 60, 120, 240, 300 and 360 minutes post $PEG_{10K}$-LysB28 insulin lispro injection; 5, 30, 60, 120, 240, 360, 540 and 720 minutes $PEG_{20K}$-LysB28 insulin lispro injection; or 5, 30, 60, 120, 240, 360, 720 and 1080 minutes post $PEG_{40K}$-LysB28 insulin lispro injection. Retro-orbital bleeds are used for any time points 5 minutes or less. At time points greater than 5 minutes, tail bleeds are used. For the last time point, blood draws are obtained by a cardiac stick. Blood is processed to serum to examine exposure by RIA (for example, Millipore) or ELISA (for example, Charles River).

Results using this method indicate that the pharmacokinetics of $PEG_{20K}$-LysB28 insulin lispro and $PEG_{40K}$-LysB28 insulin lispro are similar regardless of the animal's renal function. Comparing ⅚ nephrectomized rats with sham controls, no statistically significant impact of nephrectomy was observed on clearance of $PEG_{20K}$-LysB28 insulin lispro whereas insulin lispro clearance was reduced in ⅚ nephrectomized rats (Table I).

TABLE I

Pharmacokinetic results for insulin lispro, $PEG_{5K}$-LysB28 insulin lispro, $PEG_{10K}$-LysB28 insulin lispro, $PEG_{20K}$-LysB28 insulin lispro, and $PEG_{40K}$-LysB28 insulin lispro in 5/6 nephrectomized and sham Sprague-Dawley rats. Mean (SEM)

| Parameter | 10 nmol/kg insulin lispro[a] | | 10 nmol/kg PEG(5 kDa)-insulin lispro Model | | 10 nmol/kg PEG(10 kDa)-insulin lispro | |
|---|---|---|---|---|---|---|
| | 5/6 | Sham | 5/6 | Sham | 5/6 | Sham |
| $C_0$ (nM) | 184 (38) | 123 (31) | 189 (9) | 193 (5) | 241 (10) | 225 (18) |
| $AUC_{0-\infty}$ (nM * hr) | 15 (1.4) | 4 (0.5) | 47 (3) | 25 (1) | 143 (5) | 85 (5) |
| CL (L/hr/kg) | 0.67 (0.064) | 2.24 (0.262) | 0.22 (0.02) | 0.41 (0.02) | 0.071 (0.002) | 0.121 (0.007) |
| $V_{ss}$ (L/kg) | 0.13 (0.022) | 0.42 (0.087) | 0.131 (0.007) | 0.160 (0.004) | 0.109 (0.007) | 0.161 (0.013) |

| Parameter | 10 nmol/kg PEG(20 kDa)-insulin lispro[a] Model | | 10 nmol/kg PEG(40 kDa)-insulin lispro | |
|---|---|---|---|---|
| | 5/6 | Sham | 5/6 | Sham |
| $C_0$ (nM) | 295 (22) | 239 (22) | 410 (18) | 428 (20) |
| $AUC_{0-\infty}$ (nM * hr) | 305 (16) | 287 (19) | 1080 (46) | 1250 (33) |
| CL (L/hr/kg) | 0.033 (0.0017) | 0.035 (0.0023) | 0.0094 (0.0004) | 0.0080 (0.0002) |

TABLE I-continued

Pharmacokinetic results for insulin lispro, $PEG_{5K}$-LysB28 insulin lispro, $PEG_{10K}$-LysB28 insulin lispro, $PEG_{20K}$-LysB28 insulin lispro, and $PEG_{40K}$-LysB28 insulin lispro in 5/6 nephrectomized and sham Sprague-Dawley rats. Mean (SEM)

| | | | | |
|---|---|---|---|---|
| $V_{ss}$ (L/kg) | 0.050 (0.004) | 0.059 (0.007) | 0.046 (0.002) | 0.042 (0.002) |

[a]None of PEG(20 kDa)-insulin lispro parameters are statistically significantly different between 5/6 and sham, whereas the insulin lispro differences in AUC, CL, and Vss are statistically significant (p < 0.0001)

Abbreviations:
$C_0$ = Concentration at time zero;
$AUC_{0-\infty}$ = Area under the concentration-time curve from time zero to infinity;
CL = clearance;
$V_{ss}$ = steady-state volume of distribution.

Example 2

Clinical Studies in Renal-Impaired Patients

The pharmacokinetics after subcutaneous administration of $PEG_{20\ kDa}$-LysB28 insulin lispro are evaluated in clinical subjects with mild, moderate, or severe renal impairment, or end-stage renal disease (ESRD) versus those with normal renal function. Subjects were assigned to Groups 1 through 4 (Table II) based on an estimated creatinine clearance (CrCl) at screening as calculated using the Cockcroft-Gault equation (Cockcroft D W, Gault M H. Prediction of creatinine clearance from serum creatinine. Nephron. 1976; 16(1):31-41):

CrCl (mL/min)=(140−age)×(weight in kg)/72×(serum creatinine in mg/dL)　　Men

CrCl (mL/min)=0.85×[(140−age)×(weight in kg)/72×(serum creatinine in mg/dL)]　　Women

TABLE II

Classification of patients by renal function using the Cockcroft-Gault equation.

| Group | Classification of Renal Function | CrCl (mL/min) |
|---|---|---|
| Group 1 | CONTROL (normal renal function) | >80 |
| Group 2 | MILD renal impairment | 51-80 |
| Group 3 | MODERATE renal impairment | 30-50 |
| Group 4 | SEVERE renal impairment | <30 |
| Group 5 | ESRD | Dialysis for more than 3 months |

Abbreviations: CrCl = estimated creatinine clearance; ESRD = end-stage renal disease.
Regulatory Guidance: FDA 1998; EMEA 2004

The clinical design plan is exemplified in FIG. 1. For the "Inpatient Period," subjects are admitted to the Clinical Research Unit (CRU) on Day −1 and reside in the CRU until at least 48 hours after dosing. Subjects receive a single subcutaneous dose of $PEG_{20kDa}$-LYSB28 insulin lispro (3 nmol/kg [0.33 U/kg]) on day 1. Blood samples for pharmacokinetic analysis are collected as follows (hours post-dose): 0, 2, 4, 6, 8, 12 hours (Day 1); 24 and 36 hours (Day 2); 48 hours (Day 3); 72 hours (Day 4); 120 hours (Day 6); 168 hours (day 8); 216 hours (day 10); and 264 hours (Day 12). For hemodialysis patients, i.e., only for subjects with ESRD, the $PEG_{20kDa}$-LYSB28 insulin lispro dose is given approximately 48 hours before subjects with ESRD resume dialysis; dialysate samples are collected before dialysis is started and at 1, 2, 3, and 4 hours after the start of dialysis.

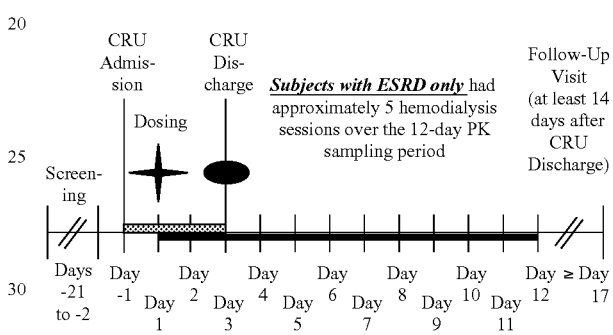

The baseline characteristics of patients in the study are presented in Table II. Serum samples are analyzed for $PEG_{20kDa}$-LYSB28 insulin lispro using a validated enzyme-linked immunosorbent assay (ELISA) method. The lower limit of quantification is 20.00 pM, and the upper limit of quantification is 500.00 pM. Samples above the upper limit of quantification are diluted and reanalyzed to yield results within the calibrated range. The individual PK analysis of serum $PEG_{20kDa}$-LYSB28 insulin lispro concentrations as a function of time are analyzed by conventional noncompartmental PK analysis using WinNonlin® Enterprise Edition software (Version 5.3, Pharsight Corporation, St. Louis, Mo., USA). The primary PK parameters determined from the concentration-time data included half-life associated with the terminal rate constant ($t_{1/2}$), area under the concentration versus time curve from time zero to infinity [$AUC_{(0-\infty)}$], and maximum observed drug concentration ($C_{max}$). The AUC values are calculated by the linear/log trapezoidal method, where the linear trapezoidal method is employed up to $t_{max}$, and the log trapezoidal rule is used for concentrations beyond $t_{max}$. The dose-normalized $C_{max}$ and $AUC_{(0-\infty)}$ are calculated for each group of subjects. Additional PK parameters include the following: apparent total body clearance of drug calculated after extra-vascular administration (CL/F), the fraction of elimination by dialysis, and the fraction of elimination by dialysis is calculated for subjects in the ESRD group as follows (Amdisen A, Skjoldborg H. Hemodialysis for lithium poisoning. Lancet. 1969; 2(7613):213):

$$\text{Fraction of Dialysis Elimination} = \frac{([\text{Observed } PEG_{20kDa} - LYSB28 \text{ insulin lispro concentration}], \text{pre-dialysis} - [\text{Extrapolated } PEG_{20kDa} - LYSB28 \text{ insulin lispro concentration}], \text{pre-dialysis})}{([\text{Observed } PEG_{20kDA} - LYSB28 \text{ insulin lispro concentration}], \text{pre-dialysis})}$$

The extrapolated pre-dialysis PK concentration is derived from the linearly fit line on the semi-logarithmic scale of the terminal phase. To eliminate potential variation by using different types of dialysis membranes, only high-flux polysulfone membranes are used.

half-life ($t_{1/2}$) is statistically similar across the cohorts. Table III summarizes the pharmacokinetic parameters for subjects. These results support that the pharmacokinetics of $PEG_{20\ kDa}$-LysB28 insulin lispro are similar regardless of a subjects' renal classification.

TABLE II

Patient demographics and baseline properties.

| Demographic and Baseline Characteristic [Mean (SD), N, or N (%)] | Estimated Creatinine Clearance (CrCl, mL/min) | | | | | |
|---|---|---|---|---|---|---|
| | Normal Function (>80) | Mild Impairment (51-80)[b] | Moderate Impairment (30-50)[c] | Severe Impairment (<30)[d] | ESRD (Dialysis for >3 mo)[e] | Overall[f] |
| N (M/F) | 12 (9/3) | 8 (7/1) | 8 (5/3) | 9 (4/5) | 9 (6/3) | 46 (31/15) |
| Age (years) | 45.5 (15.3) | 66.9 (8.9) | 61.0 (13.3) | 61.8 (11.5) | 44.4 (10.7) | 54.9 (15.1) |
| CrCl[a] (mL/min) | 122.2 (26.5) | 63.4 (6.7) | 39.4 (6.7) | 21.9 (6.9) | 13.3 (5.0) | — |
| BMI (kg/m²) | 26.7 (3.1) | 28.8 (3.9) | 27.1 (5.7) | 24.7 (3.0) | 26.5 (6.3) | 26.7 (4.5) |
| Weight (kg) | 81.3 (15.1) | 84.5 (13.0) | 73.7 (16.0) | 66.7 (10.1) | 79.9 (19.3) | 77.4 (15.7) |

Abbreviations:
BMI = body mass index;
CrCl = estimated creatnine clearance;
ESRD = end-stage renal disease;
F = female;
M = male;
N = number of subjects;
SD = standard deviation.
[a]The Cockcroft-Gault equation may not be an accurate representation of the subject's CrCl if the subject was anuric or in renal failure.
[b]Mild renal impairment group included 3 subjects with type 2 diabetes mellitus (mean duration of diabetes: 14 years).
[c]Moderate renal impairment group included 2 subjects with type 2 diabetes mellitus (mean duration of diabetes: 20 years).
[d]Severe renal impairment group included 4 subjects with type 2 diabetes mellitus (mean duration of diabetes: 25 years).
[e]ESRD group included 2 subjects with type 2 diabetes mellitus (mean duration of diabetes: 12 years).
[f]Forty-six subjects received $PEG_{20\ kDa}$-LYSB28 insulin lispro; 45 subjects completed the study and 1 subject from the SEVERE group discontinued the study due to an SAE (angina pectoris) judged to be unrelated to study treatment.

The time-course profile of serum $PEG_{20\ kDa}$-LysB28 insulin lispro following a single dose of $PEG_{20\ kDa}$-LysB28 insulin lispro is statistically similar in each cohort of subjects. The

TABLE III

Serum PEGylated Insulin Lispro Pharmacokinetic Parameters Following Single Subcutaneous Dose of 2.9 nmol/kg to subjects with Normal Renal Function, Mild Renal Impairment, Moderate Renal Impairment, Severe Renal Impairment, and ESRD.

| | Geometric Mean (CV % Geometric Mean) Serum PEGylated Insulin Lispro | | | | |
|---|---|---|---|---|---|
| | Normal Renal Function | Mild Renal Impairment | Moderate Renal Impairment | Severe Renal Impairment | ESRD |
| N | 10 | 8 | 8 | 8 | 9 |
| $C_{max}$ (pmol/L) | 1700 (77) | 2090 (88) | 1310 (29) | 1030 (77) | 1180 (124) |
| Dose-normalized $C_{max}$ (pmol/L/pmol) | 0.00713 (78) | 0.00863 (79) | 0.00623 (37) | 0.00532 (68) | 0.00518 (155) |
| $t_{max}$[a] (hr) | 12.00 (6.00-48.00) | 12.00 (8.00-36.00) | 24.01 (8.00-36.00) | 30.00 (12.00-72.00) | 24.00 (2.38-50.02) |
| $t_{1/2}$ (hr) | 34.9 (50) | 37.2 (31) | 43.7 (48) | 42.4 (16) | 45.7 (24) |
| AUC(0-∞) (pmol·hr/L) | 84100 (32) | 110000 (37) | 90400 (28) | 82400 (44) | 73400 (48) |
| Dose-normalized AUC(0-∞) (pmol·hr/L/pmol) | 0.352 (36) | 0.452 (31) | 0.429 (38) | 0.424 (39) | 0.323 (61) |
| CL/F (L/hr) | 2.84 (36) | 2.21 (31) | 2.33 (38) | 2.36 (39) | 3.10 (61) |
| (L) | (61) | (45) | (80) | (47) | (75) |
| Vss/F (L) | 142 (57) | 121 (53) | 154 (39) | 171 (58) | 210 (109) |
| Fraction of Dialysis Elimination (-) | | | | | 0.128[c] (92.3) |

[a]Median (Min-Max)

Example 3

Pharmacokinetic Comparison of PEG$_{20\ KDa}$-LysB28 Insulin Lispro and PEG$_{20kDa}$-B29 Human Insulin To induce diabetes, 10-week old male Harlan Sprague Dawley rats (Harlan, Indianapolis, Ind., USA) 250-280 g body weight, are dosed intravenously (IV) via tail vein with 45 mg/kg streptozotocin (STZ) in 0.5 M citric acid, pH 4.5, three days prior to study. On the morning of study, animals meeting an inclusion criterion of blood glucose between 400-550 mg/dL receive a single SC injection of test compound at dose levels ranging from 9.3-568 nmol/kg for PEG$_{20kDa}$-LYSB28 insulin lispro. For PK determinations, blood samples are collected by tail clip into EDTA tubes for measurement of plasma human insulin or PEG$_{20kDa}$-LYSB28 insulin lispro Immunoreactive insulin concentrations in the rat plasma are determined using a total insulin RIA. The PK of PEG$_{20kDa}$-LysB29 human insulin in STZ-treated diabetic rats are compared to that of PEG$_{20kDa}$-LysB28 insulin lispro via subcutaneous administration. Dose-response studies are performed for both compounds over a dose range of 9.3-568 nmol/kg, and under both monomeric ("mono") and hexameric ("hex") formulation conditions, PBS and Zn/m-cresol, respectively (Table IV). Graphical and noncompartmental PK analyses are performed using SigmaPlot v11 (Systsat Software, Inc., San Jose, Calif.) and WinNonlin® Professional v5.3 (Pharsight®, St Louis, Mo., USA), respectively.

The non-compartmental PK parameters for each compound at each dose level, and for each formulation is studied. The PK profile of the two molecules under monomeric and hexameric formulation conditions are statistically similar, and support that parenteral dosing of PEG$_{20\ kDa}$-LysB28 insulin lispro and PEG$_{20kDa}$-LysB29 human insulin can be used in the treatment of CKD patients.

SEQUENCE LISTING

SEQ ID Listing

A-Chain of Insulin Lispro
SEQ ID NO: 1
GIVEQCCTSICSLYQLENYCN

B-Chain of Insulin Lispro
SEQ ID NO: 2
FVNQHLCGSHLVEALYLVCGERGFFYTKPT

B-Chain of Human Insulin
SEQ ID NO: 3
FVNQHLCGSHLVEALYLVCGERGFFYTPKT

A-Chain of Insulin Glargine
SEQ ID NO: 4
GIVEQCCTSICSLYQLENYCG

B-Chain of Insulin Glargine
SEQ ID NO: 5
FVNQHLCGSHLVEALYLVCGERGFFYTPKTRR

A-Chain of Bovine Insulin
SEQ ID NO: 6
GIVEQCCASVCSLYQLENYCN

B-Chain of Bovine Insulin
SEQ ID NO: 7
FVNQHLCGSHLVEALYLVCGERGFFYTPKA

B-Chain of Des-B30 Insulin
SEQ ID NO: 8
FVNQHLCGSHLVEALYLVCGERGFFYTPK

B-Chain of Insulin Aspart
SEQ ID NO: 9
FVNQHLCGSHLVEALYLVCGERGFFYTDKT

B-Chain of Insulin Glulisine
SEQ ID NO: 10
FVKQHLCGSHLVEALYLVCGERGFFYTPET

TABLE III

Comparison of pharmacokinetics parameters for PEG$_{20kDa}$-LysB29 human insulin and PEG$_{20kDa}$-LysB28 insulin lispro in STZ-treated rats.

| Compound | Parameter | Dose (nmol/kg) | | | |
| --- | --- | --- | --- | --- | --- |
| | | 9.3 | 56.8 | 93 | 568 |
| PEG$_{20kDa}$-LysB28 insulin lispro—mono | $C_{max}$ (nM) | 1.6 ± 0.4 | 11.4 ± 1.1 | 26.4 ± 7.0 | 281 ± 96 |
| | $T_{max}$ (hr) | 9.0 ± 3.5 | 10.5 ± 3.0 | 10.5 ± 3.0 | 12 ± 0 |
| | AUC (nM * hr) | 40.9 ± 7.5 | 228 ± 24 | 506 ± 122 | 6310 ± 1700 |
| | CL/F (L/hr/kg) | 0.23 ± 0.04 | 0.25 ± 0.03 | 0.19 ± 0.04 | 0.096 ± 0.028 |
| PEG$_{20kDa}$-LysB28 insulin lispro—hex | $C_{max}$ (nM) | 2.4 ± 0.3 | 12.4 ± 0.7 | 35 ± 12 | 323 ± 48 |
| | $T_{max}$ (hr) | 12 ± 0 | 9.0 ± 3.5 | 12 ± 0 | 12 ± 0 |
| | AUC (nM * hr) | 75.0 ± 2.5 | 281 ± 16 | 541 ± 135 | 7450 ± 340 |
| | CL/F (L/hr/kg) | 0.124 ± 0.004 | 0.20 ± 0.01 | 0.18 ± 0.04 | 0.076 ± 0.004 |
| PEG$_{20kDa}$-LysB29 human insulin—mono | $C_{max}$ (nM) | 2.3 ± 0.3 | 13.7 ± 4.8 | 41.1 ± 6.3 | 318 ± 44 |
| | $T_{max}$ (hr) | 10.5 ± 3.0 | 7.5 ± 3.0 | 12 ± 0 | 15 ± 6 |
| | AUC (nM * hr) | 69 ± 16 | 261 ± 66 | 750 ± 116 | 8390 ± 940 |
| | CL/F (L/hr/kg) | 0.14 ± 0.03 | 0.23 ± 0.05 | 0.13 ± 0.02 | 0.068 ± 0.007 |
| PEG$_{20kDa}$-LysB29 human insulin—hex | $C_{max}$ (nM) | 1.5 ± 0.1 | 9.0 ± 2.7 | 12.6 ± 3.5 | 198 ± 40 |
| | $T_{max}$ (hr) | 12 ± 0 | 9 ± 3.5 | 12 ± 0 | 12 ± 0 |
| | AUC (nM * hr) | 88 ± 66 | 220 ± 13 | 244 ± 20 | 5700 ± 1000 |
| | CL/F (L/hr/kg) | 0.14 ± 0.06 | 10.26 ± 0.02 | 10.38 ± 0.03 | 0.10 ± 0.02 |

We claim:

1. A method of treating diabetes or treating hyperglycemia in a patient having moderate to end stage chronic kidney disease, comprising administering to said patient a compound of the formula P-[(A)-(B)] wherein:

A is the A-chain of insulin lispro (SEQ ID NO:1);

B is the B-chain of insulin lispro (SEQ ID NO:2); and

P is a PEG having an average molecular weight from about 17.5 kDa to about 40 kDa, and wherein A and B are properly cross-linked, and P is attached via a covalent bond to the epsilon-amine of the lysine at position 28 of B.

2. The method of claim 1, wherein the average molecular weight of the PEG is from about 17.5 kDa to about 30 kDa.

3. The method of claim 2, wherein the average molecular weight of the PEG is from about 17.5 kDa to about 25 kDa.

4. The method of claim 3 wherein the average molecular weight of the PEG is about 20 kDa.

5. The method of claim 1 wherein the compound is

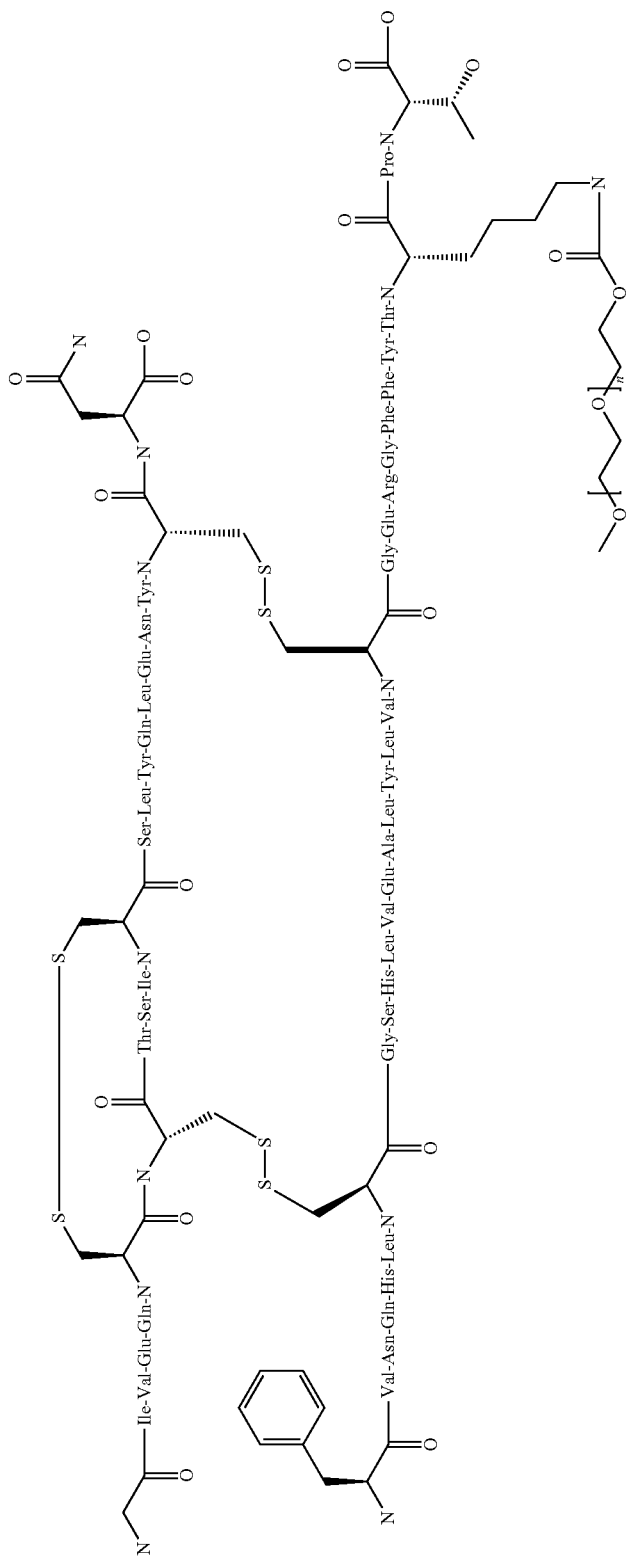

wherein the average n is 406 to 497.

6. The method of claim 5 wherein the average n is 450 to 454.

7. The method of claim 6, wherein the patient's creatinine clearance is less than 60 mL/min.

8. The method of claim 7, wherein the patient's creatinine clearance is 30 to 59 mL/min.

9. The method of claim 7 wherein the patient's creatinine clearance is 15 to 29 mL/min.

10. The method of claim 7, wherein the patient requires dialysis.

11. The method of claim 7, wherein the diabetes is type 1 diabetes.

12. The method of claim 7, wherein the diabetes is type 2 diabetes.

13. The method of claim 6, wherein the method treats insulin-induced edema.

\* \* \* \* \*